(12) United States Patent
Koizumi et al.

(10) Patent No.: US 10,863,891 B2
(45) Date of Patent: Dec. 15, 2020

(54) SIGNAL PROCESSING DEVICE AND SIGNAL PROCESSING METHOD

(71) Applicant: OLYMPUS CORPORATION, Hachioji (JP)

(72) Inventors: Yugo Koizumi, Yokohama (JP); Mai Ojima, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 659 days.

(21) Appl. No.: 15/667,725

(22) Filed: Aug. 3, 2017

(65) Prior Publication Data

US 2017/0325670 A1  Nov. 16, 2017

Related U.S. Application Data

(63) Continuation of application No. PCT/JP2015/081413, filed on Nov. 6, 2015.

(30) Foreign Application Priority Data

Feb. 10, 2015 (JP) .................... 2015-024697

(51) Int. Cl.
*A61B 1/04* (2006.01)
*A61B 1/045* (2006.01)
*A61B 1/00* (2006.01)
*G02B 23/24* (2006.01)

(52) U.S. Cl.
CPC ............ *A61B 1/041* (2013.01); *A61B 1/0002* (2013.01); *A61B 1/00006* (2013.01); *A61B 1/00009* (2013.01); *A61B 1/00057* (2013.01); *A61B 1/00059* (2013.01); *A61B 1/045* (2013.01); *G02B 23/243* (2013.01); *A61B 1/00121* (2013.01); *G02B 23/2476* (2013.01)

(58) Field of Classification Search
CPC . A61B 1/045; A61B 1/00006; A61B 1/00009; A61B 1/00002; A61B 1/00056
See application file for complete search history.

(56) References Cited

FOREIGN PATENT DOCUMENTS

| JP | 2001-087222 A | 4/2001 |
|---|---|---|
| JP | 2001-314369 A | 11/2001 |
| JP | 2005-185541 A | 7/2005 |
| JP | 2007-050108 A | 3/2007 |

OTHER PUBLICATIONS

Jan. 26, 2016 International Search Report issued in International Patent Application No. PCT/JP2015/081413.
Jan. 26, 2016 Written Opinion issued in International Patent Application No. PCT/JP2015/081413.
Dec. 6, 2016 Decision to Grant issued in Japanese Patent Application No. 2016-552544.

*Primary Examiner* — Matthew J Kasztejna
(74) *Attorney, Agent, or Firm* — Oliff PLC (57) ABSTRACT

A signal processing device includes: a connection detector that detects whether an endoscope including one or more operation members is connected; an input unit to which an operation state signal is input from an external input device including one or more buttons that correspond to the one or more operation members included in the endoscope when the endoscope is not connected; and an operation execution unit that executes an operation according to the operation state signal that is input to the input unit.

12 Claims, 6 Drawing Sheets

| ALLOCATION INFORMATION STORAGE AREA | | | |
|---|---|---|---|
|  | BUTTON A | BUTTON B | BUTTON C |
| IDENTIFICATION INFORMATION A (SCOPE A) | NBI | RELEASING | FREEZING |
| IDENTIFICATION INFORMATION B (SCOPE B) | PUMPING | ELECTRONIC MAGNIFICATION | IMAGE ENHANCEMENT |
| IDENTIFICATION INFORMATION C (SCOPE C) | FOCUSING | VIDEO RECORDING | CAPTURING |

F I G. 3

442

| REGISTER | |
|---|---|
| NBI | 00 |
| RELEASING | 00 |
| FREEZING | 00 |
| PUMPING | 00 |
| ELECTRONIC MAGNIFICATION | 00 |
| IMAGE ENHANCEMENT | 00 |
| FOCUSING | 00 |
| VIDEO RECORDING | 00 |
| CAPTURING | 00 |

SIGNAL PROCESSING DEVICE AND SIGNAL PROCESSING METHOD

CROSS-REFERENCE TO RELATED APPLICATIONS

This application is based upon and claims the benefit of priority of the prior Japanese Patent Application No. 2015-024697, filed Feb. 10, 2015, the entire contents of which are incorporated herein by reference.

This is a Continuation Application of PCT Application No. PCT/JP2015/081413, filed Nov. 6, 2015, which was not published under PCT Article 21(2) in English.

FIELD

The present invention relates to a signal processing device that an endoscope is connected to, and a signal processing method thereof.

BACKGROUND

Conventionally, endoscope systems are used in medical fields such as internal medicine or surgery. As an example, an endoscope system used in endoscopy in internal medicine (gastrointestinal medicine or the like) includes an endoscope, an endoscope video processor, a monitor device, and a peripheral device (an image recording device or the like), and the endoscope system is used in a state in which the above respective devices are connected to the endoscope video processor.

In the endoscope system used in endoscopy, a cleaned endoscope needs to be used in every endoscopy. Therefore, an endoscope used in endoscopy needs to be removed after the endoscopy, and a cleaned endoscope needs to be installed before the next endoscopy. Stated another way, an endoscope needs to be attached and detached to an endoscope video processor in every endoscopy.

In addition, in the endoscope system used in endoscopy, pre-examination preparation, such as an input of examinee data (patient data) or the like to the endoscope system or checking of an operation needed in examination of the endoscope system, is performed before endoscopy. As an example, in checking the operation of the endoscope system, an operation member (for example, a button allocated as a release button) that is included in an endoscope is operated, and operation checking is performed so as to check, for example, whether an operation according to an operation performed on the operation member (for example, a release operation) is normally performed. When there are no problems in the pre-examination preparation, endoscopy is actually started.

Under the actual situation above, pre-examination preparation cannot be completed in a state in which an endoscope is not connected to an endoscope video processor (for example, a state in which an endoscope used in the previous endoscopy has been removed and a cleaned endoscope has not yet been installed).

On the other hand, as an example, Patent Document 1 (Japanese Laid-Open Patent Publication No. 2001-87222) describes an electronic endoscope device that is capable of inputting patient data or the like and preparing for setup or the like even when an electronic endoscope is not connected to a processor device. In the electronic endoscope device, when it is determined that an electronic endoscope including a clock generator is not connected, an auxiliary clock generator on a side of the processor device, not a clock generator on a side of the electronic endoscope, is selected and used, and various functions on the side of the processor device are enabled according to a clock signal that is output from the auxiliary clock generator. Accordingly, without the electronic endoscope, patient data or the like can be input from a keyboard or the like, setup such as adjustment of a monitor can be performed, and preparation for endoscopy or the like can be performed smoothly.

In the electronic endoscope device described in Patent Document 1, various functions on the side of the processor device can be enabled (for example, setup such as adjustment of a monitor can be performed) even when the electronic endoscope is not connected to the processor device.

SUMMARY

In an aspect of the present invention, a signal processing device is provided that includes: a connection detector that detects whether an endoscope including one or more operation members is connected; an input unit to which an operation state signal is input from an external input device including one or more buttons that correspond to the one or more operation members included in the endoscope when the endoscope is not connected; an operation execution unit that executes an operation according to the operation state signal that is input to the input unit; and a reporting unit that reports an operation result of the operation execution unit.

In another aspect of the present invention, a signal processing method is provided in which a signal processing device performs: detecting whether an endoscope including one or more operation members is connected; receiving an operation state signal from an external input device including one or more buttons that correspond to the one or more operation members included in the endoscope when the endoscope is not connected; executing an operation according to the received operation state signal; and reporting an operation result.

DESCRIPTION OF EMBODIMENTS

Embodiments of the present invention are described below with reference to the drawings.

A signal processing device according to an embodiment of the present invention is included in an endoscope system used in endoscopy, for example, in internal medicine (gastrointestinal medicine or the like).

Figure 1:
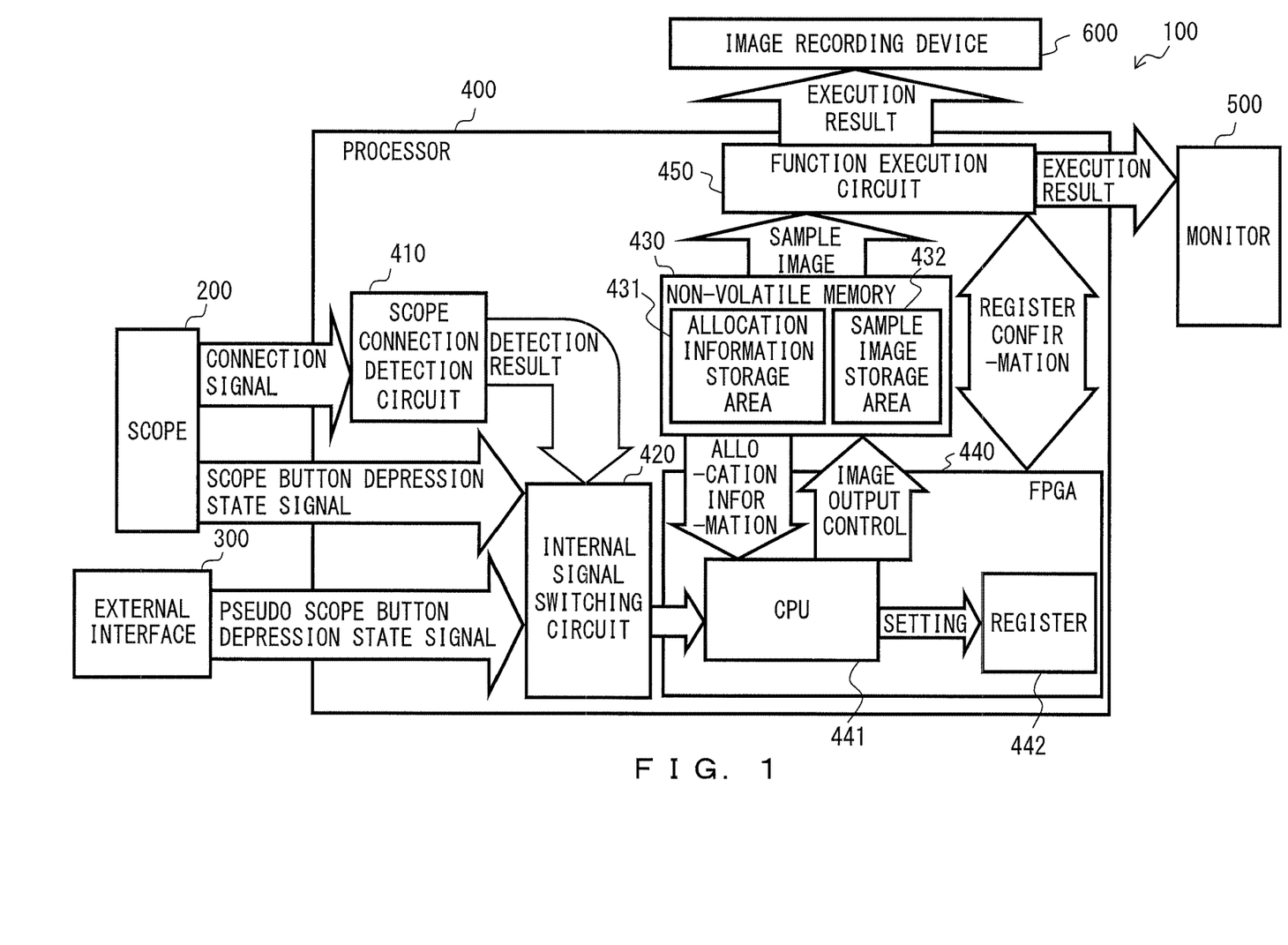
FIG. 1 illustrates an exemplary configuration of an endoscope system including an endoscope video processor that is a signal processing device according to an embodiment.

FIG. 1 illustrates an exemplary configuration of an endoscope system including an endoscope video processor that is a signal processing device according to an embodiment of the present invention.

As illustrated in FIG. 1, an endoscope system 100 includes a scope (an endoscope) 200, an external interface 300, an endoscope video processor (hereinafter simply referred to as a "processor") 400, a monitor device (hereinafter simply referred to as a "monitor") 500, and an image recording device 600, and the endoscope system 100 has a configuration in which the scope 200 and/or the external interface 300, the monitor 500, and the image recording device 600 are connected to the processor 400.

In the endoscope system 100 described above, as an example, a portion of the scope 200 is inserted into the body of an examinee, and an observation region inside the body of the examinee is imaged by the scope 200. A captured image is processed by the processor 400, and processing is performed, for example, such that the processed image is displayed on the monitor 500, or is recorded in the image recording device 600.

In the endoscope system 100, the scope 200 includes an operation unit that is operated by an examiner or the like. The operation unit includes one or more buttons, and an operation performed by the processor 400 is allocated in advance to each of the buttons. The operation allocated to each of the buttons can be changed arbitrarily. Operations that can be allocated to the respective buttons are classified into an operation that needs an image (a video signal) obtained from the scope 200 and an operation that does not need the image (the video signal) obtained from the scope 200. Examples of the former operation include freezing, releasing, capturing, marking releasing, electronic magnification, focusing, a change in the size of an image, displaying a distribution of an index of hemoglobin (IHb), image enhancement, a change in color, a change in contrast, noise reduction, picture-in-picture (PIP)/picture-on-picture (POP) display, auto gain control (AGC), and video recording. Examples of the latter operation include a change in a photometry scheme, a change in a light amount of a light source, switching display information, clocking, rotating a turret for special light observation (such as narrow band imaging (NBI), auto-fluorescence imaging (AFI), or intra-red imaging (IRI)), and feeding air (water) by using a pump.

The external interface 300 is, for example, a portable information terminal device such as a tablet terminal, or a keyboard, and the external interface 300 includes an operation unit that is operated by an examiner or the like. The operation unit includes one or more buttons that correspond to one or more buttons included in the operation unit of the scope 200, and an operation that is similar to the operation allocated to each of the buttons of the scope 200 is allocated to each of the buttons of the external interface 300. The buttons of the external interface 300 may be physical buttons, or may be virtual buttons that are realized by a touch panel or the like.

The processor 400 includes a scope connection detection circuit 410, an internal signal switching circuit 420, a non-volatile memory 430, a field-programmable gate array (FPGA) 440, and a function execution circuit 450.

The scope connection detection circuit 410 detects whether the scope 200 is connected to the processor 400 (connection or non-connection of the scope 200). Connection or non-connection is detected, for example, by detecting whether there is a connection signal that is input from the scope 200.

The internal signal switching circuit 420 switches an input signal according to a detection result of the scope connection detection circuit 410. More specifically, when the scope connection detection circuit 410 detects that the scope 200 is connected, the internal signal switching circuit 420 switches an input signal in such a way that an operation state signal that is input from the scope 200 is output to the FPGA 440. When the scope connection detection circuit 410 detects that the scope 200 is not connected, the internal signal switching circuit 420 switches an input signal in such a way that an operation state signal that is input from the external interface 300 is output to the FPGA 440. Accordingly, the internal signal switching circuit 420 selects an operation state signal that is input from the scope 200 or the external interface 300 in accordance with a detection result of the scope connection detection circuit 410, and outputs the selected operation state signal to the FPGA 440.

The operation state signal that is input from the scope 200 is a signal indicating an operation state of each of the buttons of the scope 200, and the operation state signal that is input from the external interface 300 is a signal indicating an operation state of each of the buttons of the external interface 300. The operation state of each of the buttons also refers to a depression state of each of the buttons, or the ON state or the OFF state of a switch of each of the buttons. Control is performed in such a way that an operation state signal that is input from the scope 200 when a button of the scope 200 is operated is the same as an operation state signal that is input from the external interface 300 when a button of the external interface 300 that corresponds to the button of the scope 200 is operated. Accordingly, as an example, an operation state signal that is input from the scope 200 when a button A of the scope 200 is depressed is the same as an operation state signal that is input from the external interface 300 when a buttons A' of the external interface 300 that corresponds to the button A is depressed. Thus, it can be said that an operation state signal that is input from the external interface 300 is a pseudo operation state signal that is input from the scope 200.

The non-volatile memory 430 includes an allocation information storage area 431 that stores allocation information relating to an operation that is allocated to each of the buttons of the scope 200 (this is also each of the buttons of the external interface 300), and a sample image storage area 432 that stores a sample image. The sample image is a still image or a moving image, and is also a two-dimensional image (a 2D image) or a three-dimensional image (a 3D image). The sample image is, for example, an image that is generated within the processor 400.

The FPGA 440 includes a central processing unit (CPU) 441 and a register 442.

The CPU 441 performs various types of control processing. As an example, the CPU 441 sets, in the register 442, an operation instruction (an instruction to perform or not perform each operation) according to an operation state signal that is output from the internal signal switching circuit 420, in accordance with the operation state signal and the allocation information stored in the allocation information storage area 431 of the non-volatile memory 430. In this case, when the scope connection detection circuit 410 detects that the scope 200 is not connected, and the operation instruction according to the operation state signal that is output from the internal signal switching circuit 420 is an operation instruction that needs an image obtained from the scope 200 (for example, an instruction to perform releasing or the like), the CPU 441 performs control so as to output, to the function execution circuit 450, the sample image stored in the sample image storage area 432 of the non-volatile memory 430 as the image obtained from the scope 200.

An instruction to perform or not perform each operation is set in the register 442.

The function execution circuit 450 performs an operation according to an operation instruction set by the CPU 441 of the FPGA 440. More specifically, the function execution circuit 450 monitors the register 442 of the FPGA 440, and performs an operation that has been set to be performed in the register 442. In this case, when the scope connection detection circuit 410 detects that the scope 200 is not connected, and the operation instruction that has been set in the register 442 by the CPU 441 of the FPGA 440 is an operation instruction that needs an image obtained from the scope 200 (for example, an instruction to perform releasing or the like), the function execution circuit 450 performs an operation according to the operation instruction by using a sample image that is output from the sample image storage area 432 of the non-volatile memory 430.

The monitor 500 displays an image, various types of data, or the like. As an example, the monitor 500 displays a result of the function execution circuit 450 performing an operation (success or failure in performing an operation, an image obtained by performing an operation, or the like), examinee data, or the like.

The image recording device 600 records an image, various types of data, or the like. As an example, the image recording device 600 records a result of the function execution circuit 450 performing an operation (for example, an image obtained by performing an operation), examinee data, or the like.

In the endoscope system 100 having the configuration above, the scope 200 including one or more buttons is an example of an endoscope including one or more operation members. The external interface 300 including one or more buttons that correspond to the one or more buttons of the scope 200 is an example of an external input device including one or more operation members that correspond to the one or more operation members of the endoscope. The scope connection detection circuit 410 of the processor 400 is an example of a connection detector that detects whether the endoscope including one or more operation members is connected. The internal signal switching circuit 420 of the processor 400 is an example of a signal selector that selects an operation state signal that is input from the endoscope when the connection detector detects that the endoscope is connected, and that selects an operation state signal that is input from the external input device including one or more operation members that correspond to the one or more operation members of the endoscope when the connection detector detects that the endoscope is not connected. The allocation information storage area 431 of the non-volatile memory 430 of the processor 400 is an example of an allocation information storage unit that stores allocation information relating to an operation that is allocated to each of the operation members. Some functions of the CPU 441 of the FPGA 440 of the processor 400 are examples of an operation instruction setting unit that sets an operation instruction according to an operation state signal selected by the signal selector in accordance with the operation state signal selected by the signal selector and the allocation information stored in the allocation information storage unit. The function execution circuit 450 of the processor 400 is an example of an operation execution unit that executes an operation according to the operation instruction set by the operation instruction setting unit. The sample image storage area 432 of the non-volatile memory 430 of the processor 400 is an example of a sample image storage unit that stores a sample image.

In the processor 400 of the endoscope system 100 having the configuration above, the following processing is performed, for example, at the time of checking an operation of the endoscope system 100 in pre-examination preparation for endoscopy.

First, the scope connection detection circuit 410 detects whether the scope 200 is connected to the processor 400 (connection or non-connection of the scope 200).

Then, the internal signal switching circuit 420 switches an input signal according to a detection result of the scope connection detection circuit 410. More specifically, when the scope connection detection circuit 410 detects that the scope 200 is connected, the internal signal switching circuit 420 switches an input signal in such a way that an operation state signal that is input from the scope 200 is output to the FPGA 440, and when the scope connection detection circuit 410 detects that the scope 200 is not connected, the internal signal switching circuit 420 switches an input signal in such a way that an operation state signal that is input from the external interface 300 is output to the FPGA 440.

The CPU 441 of the FPGA 440 sets, in the register 442, an operation instruction (an instruction to perform or not perform each operation) according to the operation state signal that is output from the internal signal switching circuit 420 in accordance with the operation state signal and the allocation information stored in the allocation information storage area 431 of the non-volatile memory 430. In this case, when the scope connection detection circuit 410 detects that the scope 200 is not connected, and the operation instruction according to the operation state signal that is output from the internal signal switching circuit 420 is an operation instruction that needs an image obtained from the scope 200 (for example, an instruction to perform releasing or the like), the CPU 441 performs control so as to output, to the function execution circuit 450, a sample image stored in the sample image storage area 432 of the non-volatile memory 430 as the image obtained from the scope 200.

The function execution circuit 450 that monitors the register 442 of the FPGA 440 performs an operation according to the operation instruction that has been set in the register 442 (an operation that has been set to be performed in the register 442). In this case, when the scope connection detection circuit 410 detects that the scope 200 is not connected, and the operation instruction that has been set in the register 442 by the CPU 441 of the FPGA 440 is an operation instruction that needs an image obtained from the scope 200 (for example, an instruction to perform releasing or the like), the function execution circuit 450 performs an operation according to the operation instruction by using a sample image that is output from the sample image storage area 432 of the non-volatile memory 430. An execution result of the function execution circuit 450 is displayed on the monitor 500, or is recorded in the image recording device 600.

As described above, by employing the processor 400 that is a signal processing device according to the embodiment, even in a case in which the scope 200 is not connected to the processor 400 at the time of checking an operation of the endoscope system 100 in pre-examination preparation for endoscopy, when the external interface 300 is connected to the processor 400, an operation of the processor 400 that is performed according to an operation performed on a button of the scope 200 can be performed by operating a corresponding button of the external interface 300. Accordingly, a conventional problem can be solved wherein checking an operation of the endoscope system 100 cannot be completed in pre-examination preparation because the scope 200 is not connected.

Various variations can be made to the endoscope system 100 including the processor 400 that is a signal processing device according to the embodiment.

As an example, the following variation can be made to the endoscope system 100 in such a way that an examiner or the like can freely associate a button of the external interface 300 with a desired button of a scope.

Figure 2:
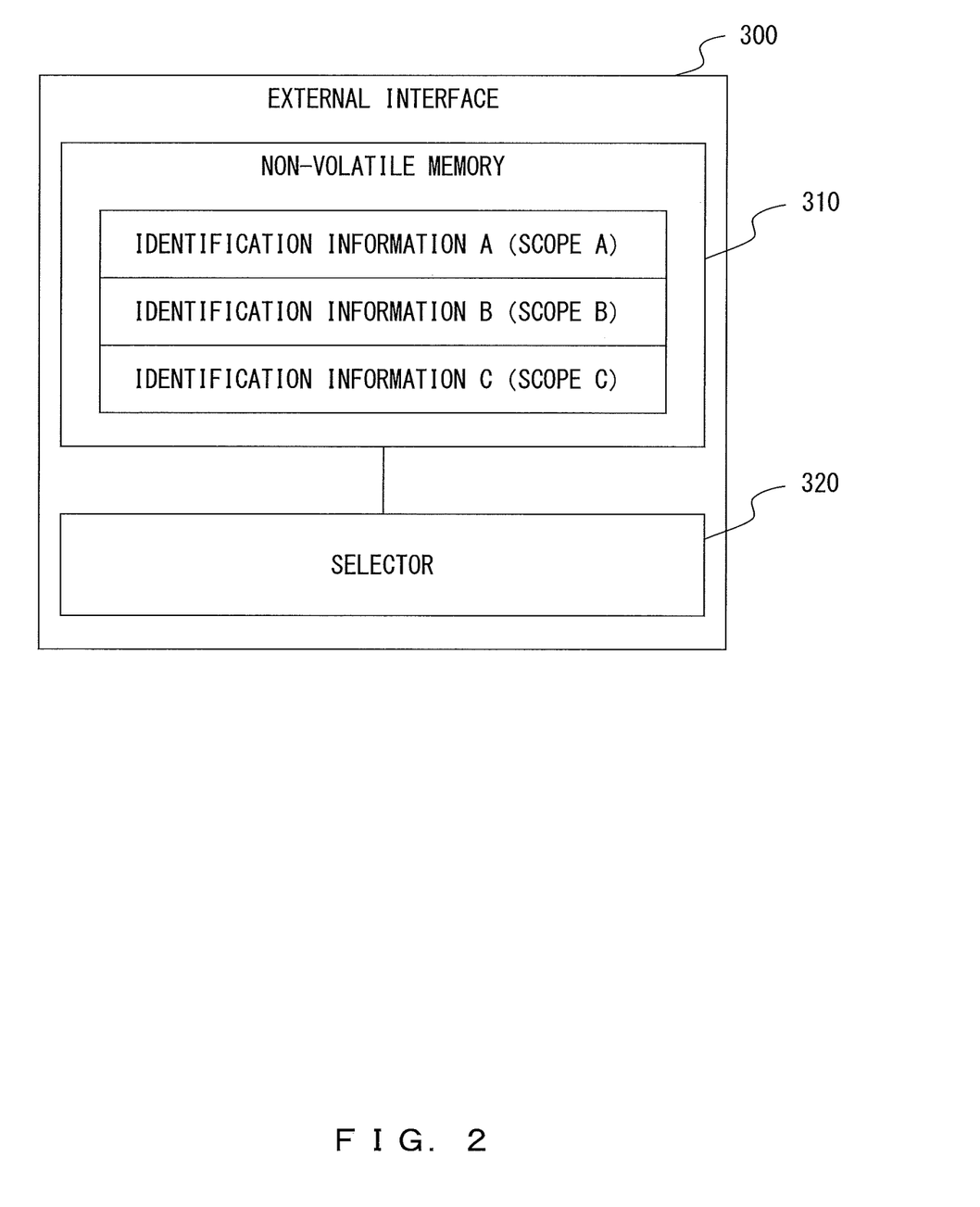
FIG. 2 illustrates an example of an external interface according to a variation.

In this case, the external interface 300 includes the non-volatile memory 310 and the selector 320, as illustrated in FIG. 2, for example. The non-volatile memory 310 stores respective pieces of identification information (identification information A, identification information B, and identification information C) of a plurality of scopes (in this example, assume that the plurality of scopes are three scopes, a scope A, a scope B, and a scope B). The selector 320 selects identification information of one scope from among respective pieces of identification information of the plurality of scopes that are stored in the non-volatile memory 310, in accordance with a prescribed operation that an examiner or the like performs on the external interface 300.

Figure 3:
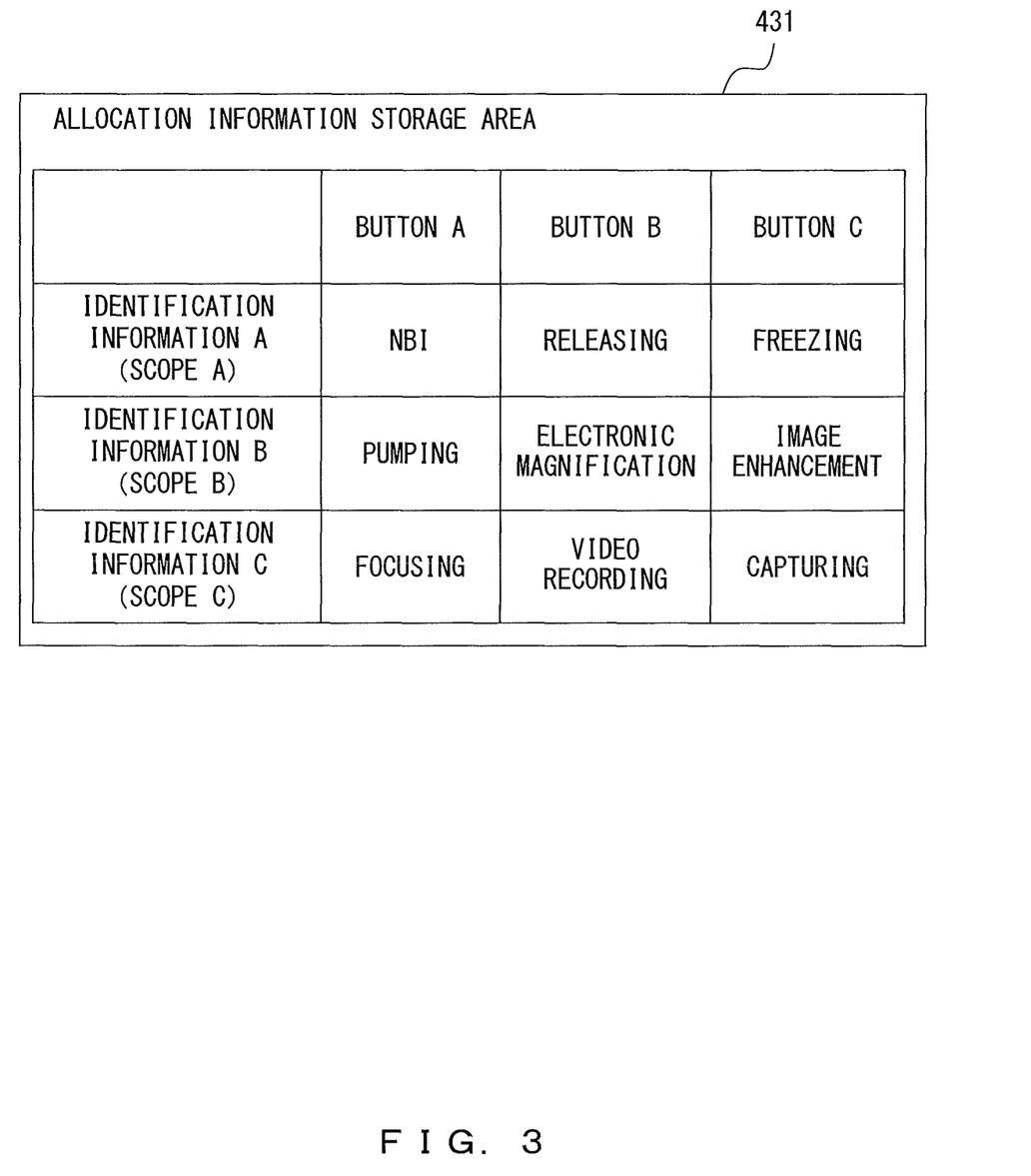
FIG. 3 illustrates an example of an allocation information storage area according to a variation.

The allocation information storage area 431 of the non-volatile memory 430 of the processor 400 stores allocation information relating to an operation that is allocated to each of the buttons for each of the pieces of identification information of the scopes, as illustrated in FIG. 3, for example. In the example illustrated in FIG. 3, NBI (rotating a turret for NBI), releasing, and freezing are respectively allocated to a button A, a button B, and a button C of the scope A that corresponds to the identification information A. Pumping, electronic magnification, and image enhancement are respectively allocated to a button A, a button B, and a button C of the scope B that corresponds to the identification information B. Focusing, video recording, and capturing are respectively allocated to a button A, a button B, and a button C of the scope C that corresponds to the identification information C.

Figure 4:
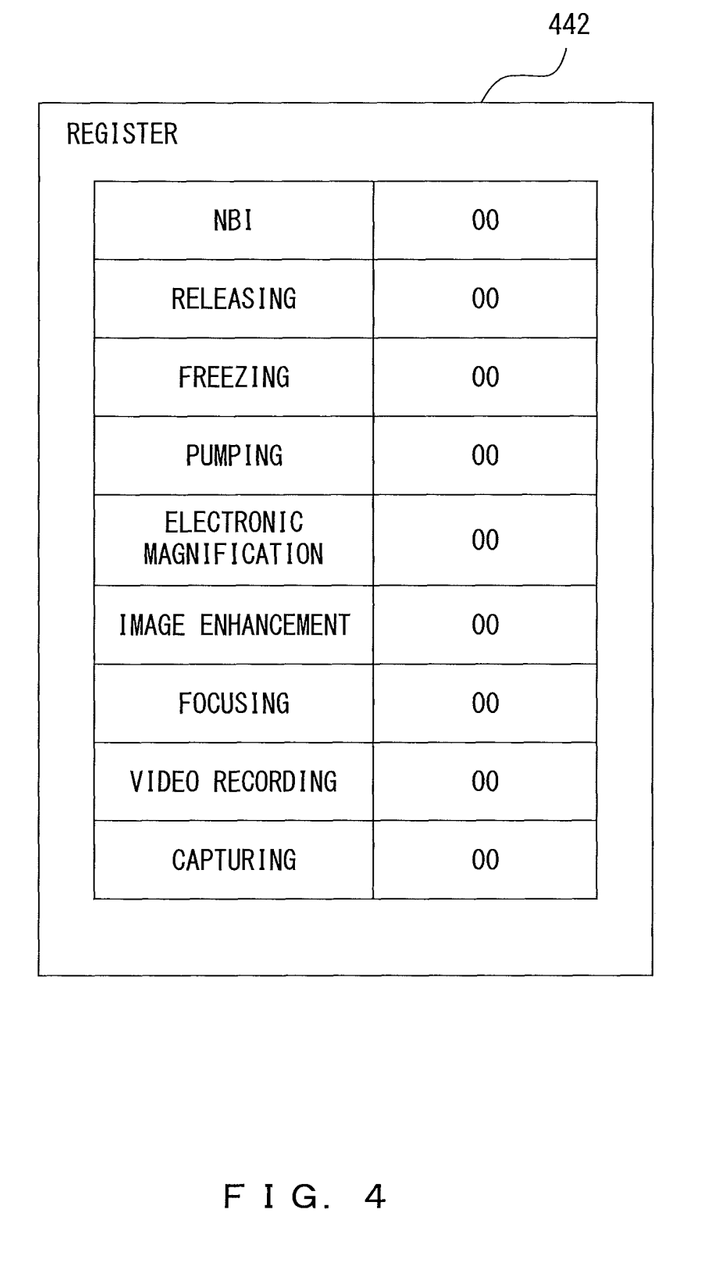
FIG. 4 illustrates an example of a register according to a variation.

An instruction to perform or not perform each operation is set in the register 442 of the FPGA 440 of the processor 400, as illustrated in FIG. 4, for example. In the example illustrated in FIG. 4, an instruction to perform or not perform each of the operations, NBI (rotating a turret for NBI), releasing, freezing, pumping, electronic magnification, image enhancement, focusing, video recording, and capturing, is set. In this example, "01" is set as an instruction to perform an operation, and "00" is set as an instruction to not perform an operation.

In the endoscope system 100 according to the variation above, in a case in which a scope is not connected to the processor 400 at the time of checking an operation of the endoscope system 100 in pre-examination preparation for endoscopy, the following processing is performed, for example.

First, in the external interface 300, the selector 320 selects identification information of a scope to be used in the next examination in accordance with a prescribed operation performed by an examiner or the like. The selected identification information of the scope is reported to the CPU 441 of the FPGA 440 of the processor 400.

In the processor 400, the scope connection detection circuit 410 detects that a scope is not connected to the processor 400 (non-connection of a scope).

Then, the internal signal switching circuit 420 switches an input signal according to a detection result (non-connection of a scope) of the scope connection detection circuit 410 in such a way that an operation state signal that is input from the external interface 300 is output from the FPGA 440.

The CPU 441 of the FPGA 440 sets, in the register 442, an operation instruction of a scope of corresponding identification information (an instruction to perform or not perform an operation that is allocated to each of the buttons of the scope of the corresponding identification information) according to the operation state signal that is output from the internal signal switching circuit 420 in accordance with the operation state signal, the allocation information stored in the allocation information storage area 431 of the non-volatile memory 430 (see FIG. 3), and the identification information of the scope that is reported from the external interface 300. As an example, in a case in which the identification information of the scope that is reported from the external interface 300 is the identification information A of the scope A, and a button of the external interface 300 that corresponds to the button A of the scope A is depressed, NBI in the register 442 illustrated in FIG. 4 is set to "01". As another example, in a case in which the identification information of the scope that is reported from the external interface 300 is the identification information B of the scope B, and a button of the external interface 300 that corresponds to the button B of the scope B is depressed, electronic magnification in the register 442 illustrated in FIG. 4 is set to "01". In this case, in a case in which an operation instruction according to the operation state signal that is output from the internal signal switching circuit 420 is an operation instruction that needs an image obtained from a scope (for example, an instruction to perform the above electronic magnification or the like), the CPU 441 performs control so as to output, to the function execution circuit 450, a sample image stored in the sample image storage area 432 of the non-volatile memory 430 as the image obtained from a scope.

The processing that follows is as described above, and its description is omitted.

According to the variation above, an examiner or the like can freely associate a button of the external interface 300 with a desired button of a scope, and can make the processor 400 perform an operation according to an operation that is performed on the desired button of the scope by operating the button of the external interface 300.

In this variation, the non-volatile memory 310 of the external interface 300 is an example of an endoscope identification information storage unit that stores respective pieces of endoscope identification information of a plurality of endoscopes. The selector 320 of the external interface 300 is an example of an endoscope identification information selector that selects one piece of endoscope identification information from among plural pieces of endoscope identification information stored in the endoscope identification information storage unit.

In the processor 400 that is a signal processing device according to the embodiment, a further variation may be made in such a way that the CPU 441 of the FPGA 440 performs the following processing, for example, in order to reduce a load on an examiner or the like at the time of checking an operation of the endoscope system 100 in pre-examination preparation.

Figure 5:
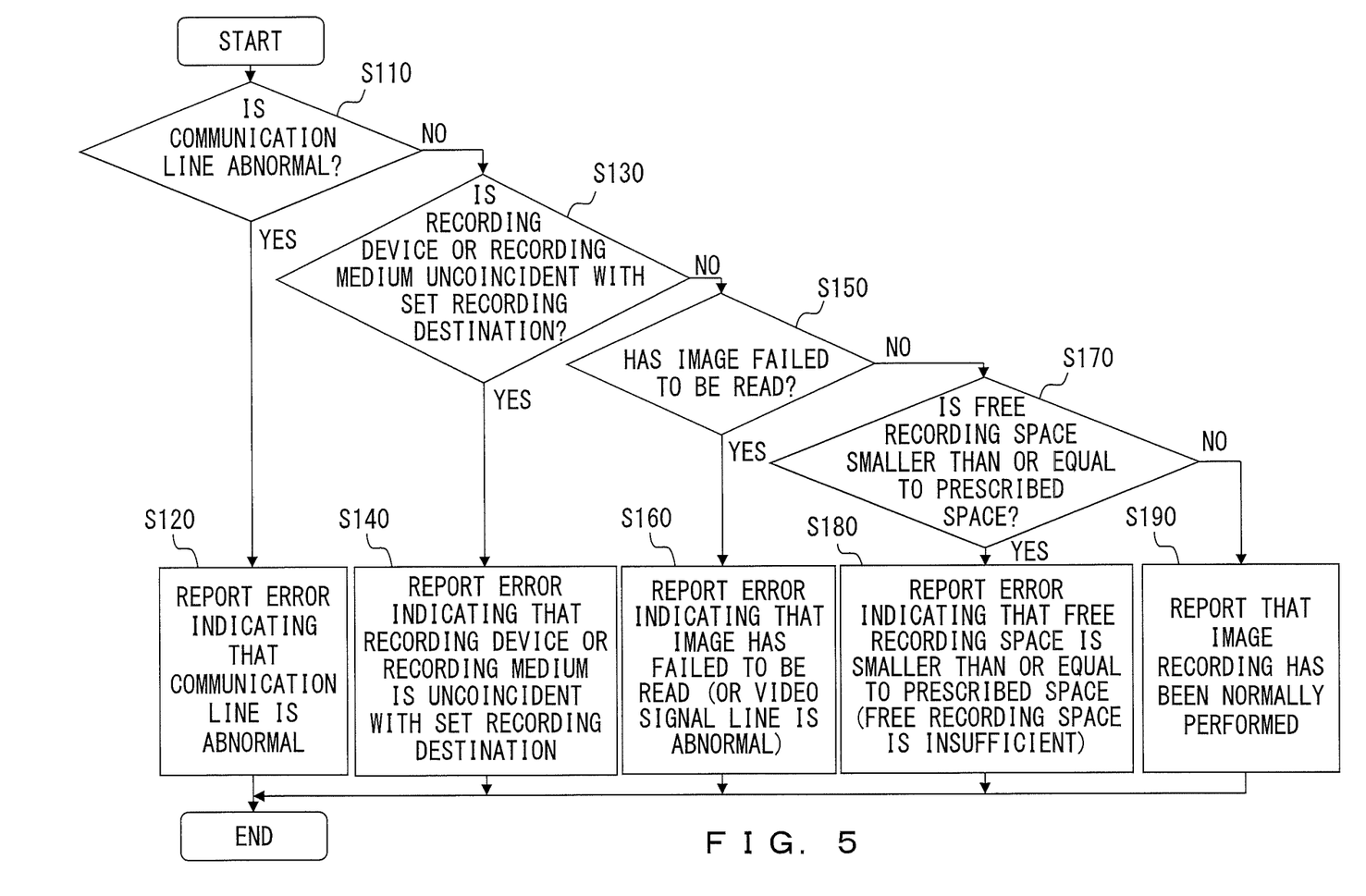
FIG. 5 is a flowchart illustrating an example of the processing content of a CPU according to a variation.

FIG. 5 is a flowchart illustrating an example of the processing content. This processing is processing that is started, for example, after the function execution circuit 450 performs an operation including an image recording operation (for example, releasing, capturing, recording, and the like) at the time of checking an operation of the endoscope system 100 in pre-examination preparation.

As illustrated in FIG. 5, when this processing is started, the CPU 441 first determines whether a communication line (a communication path) to a recording device or a recording medium that is connected to the processor 400 is abnormal (S110). The recording device that is connected to the processor 400 is, for example, the image recording device 600 above, or a recording device that is connected to the processor 400 via a network. The recording medium that is connected to the processor 400 is, for example, a universal serial bus (USB) memory. As an example, when communication can be performed between the recording device or recording medium that is connected to the processor 400 and the processor 400, the determination result in S110 is No, and otherwise the determination result is Yes. In a case in which the recording medium that is connected to the processor 400 is a recording medium that does not have a communication function (for example, a USB memory that does not have a communication function), the determination result in S110 is regarded as No, and processing is proceeded.

When the determination result in S110 is Yes, the CPU 441 performs control so as to display, on the monitor 500, an error report indicating that a communication line between the recording device or recording medium that is connected to the processor 400 and the processor 400 is abnormal (S120).

When the determination result in S110 is No, the CPU 441 determines whether the recording device or recording medium that is connected to the processor 400 is uncoincident with a recording device or recording medium that has been set to be an image recording destination in the processor 400 (S130). As an example, when the image recording device 600 is connected to the processor 400, in a case in which a USB memory has been set to be an image recording destination in the processor 400, both are uncoincident with each other, and therefore the determination result is Yes.

When the determination result in S130 is Yes, the CPU 441 performs control so as to display, on the monitor 500, an error report indicating that the recording device or recording medium that is connected to the processor 400 is uncoincident with a recording device or recording medium that has been set to be an image recording destination in the processor 400 (S140).

When the determination result in S130 is No, the CPU 441 determines whether an image has failed to be read from the recording device or recording medium that is connected to the processor 400 (S150). In a case in which the recording device or recording medium that is connected to the processor 400 is connected to the processor 400 via a communication line and a video signal line, it is determined in S150 whether the video signal line between the recording device or recording medium that is connected to the processor 400 and the processor 400 is abnormal.

When the determination result in S150 is Yes, the CPU 441 performs control so as to display, on the monitor 500, an error report indicating that an image has failed to be read from the recording device or recording medium that is connected to the processor 400 (or an error report indicating that the video signal line between the recording device or recording medium that is connected to the processor 400 and the processor 400 is abnormal) (S160).

When the determination result in S150 is No, the CPU 441 determines whether a free recording space of the recording device or recording medium that is connected to the processor 400 is smaller than or equal to a prescribed space (S170). The prescribed space is a recording space that is smaller than a recording space that is needed for at least one endoscopy.

When the determination result in S170 is Yes, the CPU 441 performs control so as to display, on the monitor 500, an error report indicating that the free recording space of the recording device or recording medium that is connected to the processor 400 is smaller than or equal to a prescribed space (an error report indicating that a free recording space is insufficient) (S180).

When the determination result in S170 is No, the CPU 441 performs control so as to display, on the monitor 500, a report indicating that image recording has been normally performed (S190).

After S120, S140, S160, S180, or S190, this processing is finished.

According to the variation above, an examiner or the like can easily specify the cause of failure in image recording at the time of checking an operation of the endoscope system 100 in pre-examination preparation, and a load on the examiner or the like at the time of checking the operation of the endoscope system 100 can be reduced.

In this variation, a function of the CPU 441 for performing the processing illustrated in FIG. 5 is an example of a determination unit that performs any one or more of first determination of whether a communication path to a connected recording device or recording medium is abnormal, second determination of whether the connected recording device or recording medium is uncoincident with a recording device or recording medium that has been set to be an image recording destination, third determination of whether an image has failed to be read from the connected recording device or recording medium, and fourth determination of whether a free recording space of the connected recording device or recording medium is smaller than or equal to a prescribed space, at the time of operation checking. The monitor 500 is an example of an error reporting unit that reports an error when a result of any one of the first determination to the fourth determination performed by the determination unit is true.

In this variation, as an example, the CPU 441 of the FPGA 440 may perform control so as to store a determination result of determination processing performed in the flowchart of FIG. 5 in a determination result storage area included in the non-volatile memory 430, and may further perform the following processing.

Figure 6:
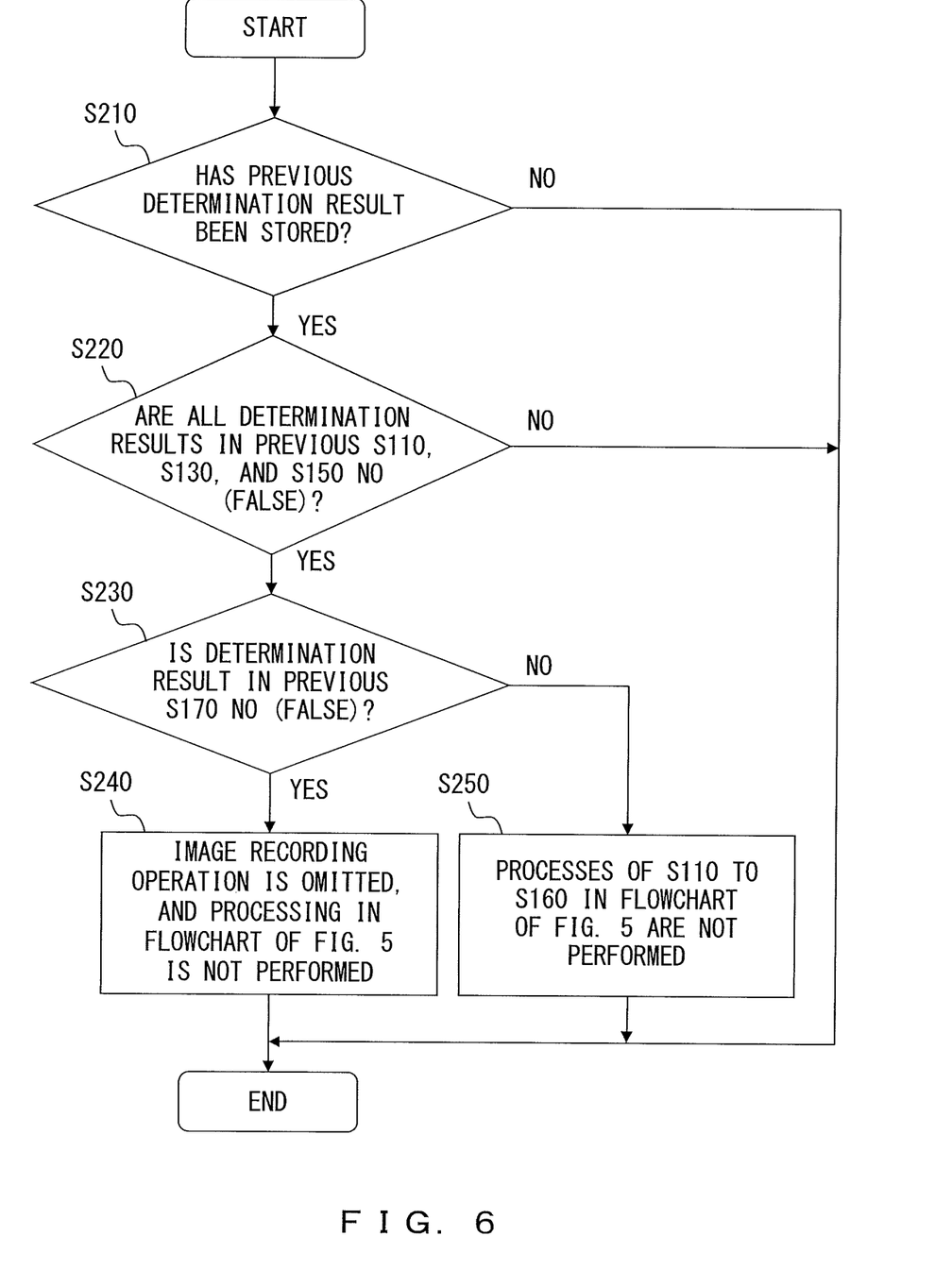
FIG. 6 is a flowchart illustrating an example of the processing content of a CPU according to a variation.

FIG. 6 is a flowchart illustrating an example of the processing content. This processing is processing that is started, for example, before the function execution circuit 450 performs an operation including an image recording operation at the time of checking an operation of the endoscope system 100 in pre-examination preparation.

As illustrated in FIG. 6, when this processing is started, the CPU 441 first determines whether a previous determination result has been stored in the determination result storage area of the non-volatile memory 430 (S210).

When the determination result in S210 is Yes, the CPU 441 determines whether all of the determination results in the previous S110, S130, and S150 are No (false) in accordance with the previous determination result stored in the determination result storage area of the non-volatile memory 430 (S220).

When the determination result in S220 is Yes, the CPU 441 determines whether a determination result in the previous S170 is No (false) in accordance with the previous determination result stored in the determination result storage area of the non-volatile memory 430 (S230).

When the determination result in S230 is Yes, the CPU 441 controls the function execution circuit 450 to omit an image recording operation from an operation including the image recording operation that the function execution circuit 450 will perform next time, and also controls the function execution circuit 450 to not perform the processing in the flowchart illustrated in FIG. 5 after an operation in which the image recording operation is omitted (S240).

When the determination result in S230 is No, the CPU 441 performs control to omit the processes of S110 to S160 and to perform only the processes of S170 to S190 in the processing in the flowchart illustrated in FIG. 5 that is performed after an operation including the image recording operation that the function execution circuit 450 will perform next time (S250). Namely, the CPU 441 performs control to only determine a free recording space and perform processing according to a determination result.

When the determination result in S210 is No, when the determination result in S220 is No, when the process of S240 is performed, or when the process of S250 is performed, this processing is finished. When the determination result in S210 is No, or when the determination result in S220 is No, the operation including the image recording operation that the function execution circuit 450 will perform next time is performed with no change, and the processing in the flowchart illustrated in FIG. 5 that is performed after the operation including the image recording operation is also performed with no change.

In the processing above, at the time of checking an operation of the endoscope system 100 in pre-examination preparation, an examiner or the like does not need to confirm the image recording operation or to confirm a free recording space of a recording device or recording medium that is connected to the processor 400 every time an operation including the image recording operation is performed. Accordingly, a load on the examiner or the like at the time of checking the operation of the endoscope system 100 can be reduced. In addition, the time needed to check the operation of the endoscope system 100 can be reduced.

In this variation, the determination result storage area included in the non-volatile memory 430 of the processor 400 is an example of a determination result storage unit that stores a result of any one or more of the first determination to the fourth determination performed by the determination unit.

In addition, a plurality of recording destinations, such as a plurality of recording devices or a plurality of recording media, or one or more recording devices and one or more recording media, may be connected as image recording destinations to the processor 400 that is a signal processing device according to the embodiment. In this case, the operation above that is performed on one recording destination (for example, the image recording device 600) may be performed on each of the connected recording destinations.

The processor 400 that is a signal processing device according to the embodiment may be configured to be integrated with the external interface 300. In this case, the external interface 300 is configured to be, for example, a front panel of the processor 400.

The embodiment described above gives a specific example of the present invention in order to make the invention easily understandable, and the present invention is not limited to the embodiment described above. Various variations or modifications can be made to the present invention without departing from the spirit of the present invention specified in the claims.

What is claimed is:

1. A signal processing device comprising:
a connection detector that detects whether an endo scope including one or more operation members is connected to the signal processing device, each of the one or more operation members corresponding to a function performed by the endoscope;
an input unit to which an operation state signal that corresponds to one of the one or more operation members is input (1) from the endoscope when the connection detector detects that the endoscope is connected and (2) from an external input device including one or more buttons that correspond to the one or more operation members included in the endoscope when the endoscope is not connected;
an operation execution unit that executes an operation according to the operation state signal that is input to the input unit; and
a reporting unit that reports an operation result of the operation execution unit.

2. The signal processing device according to claim 1, wherein:
the input unit is configured to receive a plurality of the operation state signal; and
the plurality of the operation state signal that are input from the external input device are signals that indicate the same operations as operations indicated by the plurality of operation state signal from the one or more operation members included in the endoscope.

3. The signal processing device according to claim 1, further comprising:
a signal selector that selects the operation state signal that is input from the endoscope when the connection detector detects that the endoscope is connected, and that selects the operation state signal that is input from the external input device when the connection detector detects that the endoscope is not connected, wherein
the operation execution unit executes the operation according to the operation state signal selected by the signal selector.

4. The signal processing device according to claim 3, further comprising:
an allocation information storage unit that stores allocation information relating to an operation that is allocated to the each of the one or more operation members; and
an operation instruction setting unit that sets an operation instruction according to the operation state signal selected by the signal selector and the allocation information stored in the allocation information storage unit, wherein
the operation execution unit executes the operation according to the operation instruction set by the operation instruction setting unit.

5. The signal processing device according to claim 4, further comprising:
a sample image storage unit that stores a sample image, wherein
when the connection detector detects that the endoscope is not connected, and the operation instruction set by the operation instruction setting unit needs an image from the endoscope, the operation execution unit executes the operation according to the operation instruction by using the sample image stored in the sample image storage unit.

6. The signal processing device according to claim 4, wherein
the external input device includes:
an endoscope identification information storage unit that stores endoscope identification information of each of a plurality of endoscopes; and
an endoscope identification information selector that selects the endoscope identification information for one of the plurality of endoscopes from the endoscope identification information storage unit,
the allocation information storage unit stores the allocation information relating to the operation that is allocated to the each of the one or more operation members for the each of the plurality of endo scopes, and
when the connection detector detects that the endoscope is not connected, the operation instruction setting unit sets the operation instruction corresponding to the endoscope identification information for the one of the plurality of endoscopes according to the operation state signal selected by the signal selector, the allocation information stored in the allocation information storage unit, and the endoscope identification information selected by the endoscope identification information selector, the endoscope identification information being input from the external input device.

7. The signal processing device according to claim 1, further comprising:
a determination unit that, at a time of operation checking, performs any one or more of first determination of whether a communication path to a connected recording device or recording medium is abnormal, second determination of whether the connected recording device or recording medium is uncoincident with a recording device or recording medium that is set in advance to be an image recording destination, third determination of whether an image has failed to be read from the connected recording device or recording medium, and fourth determination of whether a free recording space of the connected recording device or recording medium is smaller than or equal to a prescribed space.

8. The signal processing device according to claim 7, further comprising:
an error reporting unit that reports an error when a result of any one of the first determination to the fourth determination performed by the determination unit is true.

9. The signal processing device according to claim 7, further comprising:
a determination result storage unit that stores a result of any one or more of the first determination to the fourth determination performed by the determination unit.

10. The signal processing device according to claim 9, wherein
at a time of operation checking, when all results of a previous first determination to a previous fourth determination that are stored in the determination result storage unit are false, an image recording operation is omitted from an operation including the image recording operation that the operation execution unit will execute next time.

11. The signal processing device according to claim 9, wherein
at the time of operation checking, when all results of the previous first determination to a previous third determination that are stored in the determination result storage unit are false, and when a result of the previous fourth determination is true, the first determination to the third determination are not performed, but the fourth determination is performed in a next determination performed by the determination unit.

12. A signal processing method performed by a signal processing device, the signal processing method comprising:
detecting whether an endoscope including one or more operation members is connected to the signal processing device, each of the one or more operation members corresponding to a function performed by the endoscope;
receiving an operation state signal from (1) the endoscope when the endoscope is connected to the signal processing device and (2) an external input device including one or more buttons that correspond to the one or more operation members included in the endoscope when the endoscope is not connected;
executing an operation according to the received operation state signal; and
reporting an operation result.

* * * * *